(12) United States Patent
Choi et al.

(10) Patent No.: US 8,311,642 B2
(45) Date of Patent: Nov. 13, 2012

(54) ADJUSTABLE IMPLANT ELECTRODE SYSTEM AND IMPLANT ELECTRODE ASSEMBLY THEREOF

(75) Inventors: Charles Tak-Ming Choi, Hsinchu (TW); Chien-Hua Hsu, Jhubei (TW)

(73) Assignee: National Chiao Tung University, Hsinchu (TW)

( * ) Notice: Subject to any disclaimer, the term of this patent is extended or adjusted under 35 U.S.C. 154(b) by 513 days.

(21) Appl. No.: 12/587,252

(22) Filed: Oct. 5, 2009

(65) Prior Publication Data
US 2010/0125311 A1 May 20, 2010

(30) Foreign Application Priority Data
Nov. 18, 2008 (TW) .............................. 97144602 A

(51) Int. Cl.
*A61F 11/04* (2006.01)
(52) U.S. Cl. .................. 607/116; 607/1; 607/2; 607/45; 607/55; 607/56; 607/57; 607/61; 607/62; 607/65; 607/115; 607/118; 607/136; 607/137; 607/139; 607/149
(58) Field of Classification Search .................. 607/1–2, 607/45, 55–57, 61–62, 65, 115–116, 118, 607/136, 137, 139, 149; 128/899; 600/12–13
See application file for complete search history.

(56) References Cited

U.S. PATENT DOCUMENTS

| | | | |
|---|---|---|---|
| 6,263,225 B1 | 7/2001 | Howard, III | |
| 6,475,223 B1 | 11/2002 | Werp et al. | |
| 2006/0052656 A1 | 3/2006 | Maghribi et al. | |
| 2006/0235500 A1* | 10/2006 | Gibson et al. | 607/137 |
| 2007/0225787 A1* | 9/2007 | Simaan et al. | 607/137 |

* cited by examiner

*Primary Examiner* — Carl H Layno
*Assistant Examiner* — Deborah Malamud
(74) *Attorney, Agent, or Firm* — Hudak, Shunk & Farine Co. LPA

(57) ABSTRACT

An adjustable implant electrode system comprises an adjustable implant electrode assembly and an adjustment device for adjusting the adjustable implant electrode assembly to a desired position. The adjustable implant electrode assembly comprises an implant, a plurality of electrodes, and a plurality of magnetic components. The electrodes are disposed in the implant for providing stimulating currents according to a control signal. The magnetic components are combined with the electrodes in one-to-one correspondence. The adjustment device comprises a control unit, an excitation unit, and one or more magnetic units. The control unit is used to select one or more magnetic components to be moved from the magnetic components, and the excitation unit is used to excite the selected one or more magnetic components for the same to generate a magnetic pole, and the magnetic unit is adapted to generate a magnetic field to drive the magnetic pole and accordingly move the implant.

18 Claims, 11 Drawing Sheets

ADJUSTABLE IMPLANT ELECTRODE SYSTEM AND IMPLANT ELECTRODE ASSEMBLY THEREOF

CROSS-REFERENCE TO RELATED APPLICATION

This application claims the benefit of Taiwan Patent Application No. 097144602, filed on Nov. 18, 2008 in the Taiwan Intellectual Property Office, the disclosure of which is incorporated herein in its entirety by reference.

FIELD OF THE INVENTION

The present invention relates to an implant electrode assembly applied to human body, and more particularly to an adjustable implant electrode assembly applied to human body.

BACKGROUND OF THE INVENTION

With the progress in the medical science and technologies, many types of artificial organs have been developed to substitute for patients' impaired organs. A human body implant electrode assembly is designed to substitute the excitation of bioelectric signals by using current stimulation, so as to correct organs that could not work normally. Among others, the technique of cochlear implantation has reached a highly matured stage. As it is known, the human ear can hear because the tympanic membrane is vibrated by acoustic waves, and the auditory ossicles transmit vibration signals to the cochlea, and then, the frequencies of vibration signals are analyzed in the cochlea to produce bioelectric signals corresponding to the bands of the auditory waves. Finally, the bioelectric signals form hearing sense at the cerebral cortex. The cochlear implant is designed based on the aforementioned concept about hearing. For this purpose, the cochlear implant includes a speech processor to convert the acoustic waves into frequency signals. The frequency signals bypass the tympanic membrane and the auditory ossicles, so that stimulating currents corresponding to different frequencies are directly fed into the cochlea to stimulate corresponding auditory nerves. That is, the normal procedures for generating bioelectric signals are replaced by the operating procedures of the cochlear implant.

The cochlear implant is an electrode array consisting of a flexible member carrying a plurality of electrodes thereon. The cochlear implant is connected to an external speech processor, which performs signal process to convert sounds into current signals. Then, the electrodes are controlled to produce stimulating currents to replace the human body's bioelectric signals and thereby reconstruct a patient's hearing. For example, in a normal condition, the apical (deep) area of the cochlea serves to process the low-frequency band of the acoustic signals. Therefore, when the speech processor has separated the low-frequency signals from the acoustic waves, the electrodes near the apical (deep) area of the cochlea are driven to produce stimulating currents to replace the bioelectric signals.

However, according to the currently available implant surgery operation and equipment, the implantation of cochlear implant is still largely relied on the microsurgery, and therefore encounters with many bottlenecks. Please refer to FIG. 1 that is a schematic view of a conventional cochlear implant, which includes a flexible implant 200. Since the human cochlea 100 is a coiled structure, when performing surgery operation to implant the flexible implant 200 into the cochlea 100, the surgeon's skill and experience are very important factors in the operation. In the event the flexible implant 200 is not correctly implanted, the fragile cochlea wall or membrane inside the cochlea is dangerously subject to lesion, as the lesioned area 300 shown in FIG. 1. Please further refer to FIG. 2 that is another schematic view of the conventional cochlear implant. Another very common problem in the cochlear implant surgery operation is that the flexible implant 200 must be very soft and is therefore frequently subject to undesirable bending in the process of implantation, as the bent portions 310 shown in FIG. 2. The bent flexible implant 200 will result in interrupted signal transmission, mutual interference between stimulating currents, incorrect electrode positions, etc. Even if the cochlear implant has been completely implanted into the cochlea, it is possible the distances between an axis of the cochlea and different portions of the flexible implant 200 are not uniform, as the non-uniformly spaced areas 320 shown in FIG. 3, which is still another schematic view of the conventional cochlear implant. The problem of non-uniformly spaced areas 320 might occur during the implant surgery operation or after strenuous exercise of the user. Due to the existence of non-uniformly spaced areas 320, the user will be particularly sensitive to sounds fallen in some frequency bands while insensitive to sounds fallen in some other frequency bands. Even if the implant surgery operation has been successfully performed, the cochlear implant will still face some other problems after being used for a period of time. For instance, electrodes for some important and often needed bands and electrodes located at positions with the auditory nerves in a relatively good condition are subject to bending or damage because these electrodes often have electric currents flowed therethrough. Under this circumstance, the patient would require another surgery operation to replace the cochlear implant. US Patent Publication No. 20060052656, U.S. Pat. No. 6,263,225B1, and U.S. Pat. No. 6,475,223B1 all disclose implant techniques relating to human body.

SUMMARY OF THE INVENTION

In view of the aforementioned conventional drawbacks, a primary object of the present invention is to provide an adjustable implant electrode system and an implant electrode assembly thereof so as to solve the foregoing problems of a human body implant electrode surgery operation.

A primary object of the present invention is to provide an adjustable implant electrode assembly, which comprises an implant, a plurality of electrodes, and a plurality of magnetic components. The electrodes are disposed in the implant for providing stimulating currents according to a control signal. The magnetic components are combined with the electrodes in one-to-one correspondence, and can each generate a magnetic pole under an excitation current. Therefore, by driving the magnetic poles through externally applied magnetic fields, it is possible to move the implant of the adjustable implant electrode assembly.

Another object of the present invention is to provide an adjustable implant electrode system, which comprises an adjustable implant electrode assembly and an adjustment device for adjusting the adjustable implant electrode assembly to a desired position. The adjustable implant electrode assembly comprises an implant, a plurality of electrodes, and a plurality of magnetic components. The electrodes are disposed in the implant for providing stimulating currents according to a control signal. The magnetic components are combined with the electrodes in one-to-one correspondence. The adjustment device comprises a control unit, an excitation unit, and one or more magnetic units. The control unit is used to select one or more magnetic components to be moved from among all the magnetic components, and the excitation unit is used to excite the selected one or more magnetic components by providing electrical current and turn the selected magnetic components into magnets, thus, generating magnetic poles, and the magnetic unit is adapted to generate a magnetic field to drive the magnetic pole and accordingly move the implant.

With the above arrangements, the adjustable implant electrode system and the adjustable implant electrode assembly of the present invention utilize magnetic fields to microadjust the positions of the electrodes and therefore possible to perform a non-invasive human body implant electrode fine adjustment operation. In addition, when the adjustable implant electrode assembly of the present invention is applied to a cochlear implant, and an electrode thereof for an important band or located at a position with the auditory nerve in a relatively good condition becomes damaged, the adjustable implant electrode system of the present invention can utilize a magnetic field to shift another adjacent electrode from a less important band or another electrode located at a position with the auditory nerve in a relatively poor condition to thereby replace the damaged electrode. Therefore, it is not necessary to perform the cochlear implant surgery operation again.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
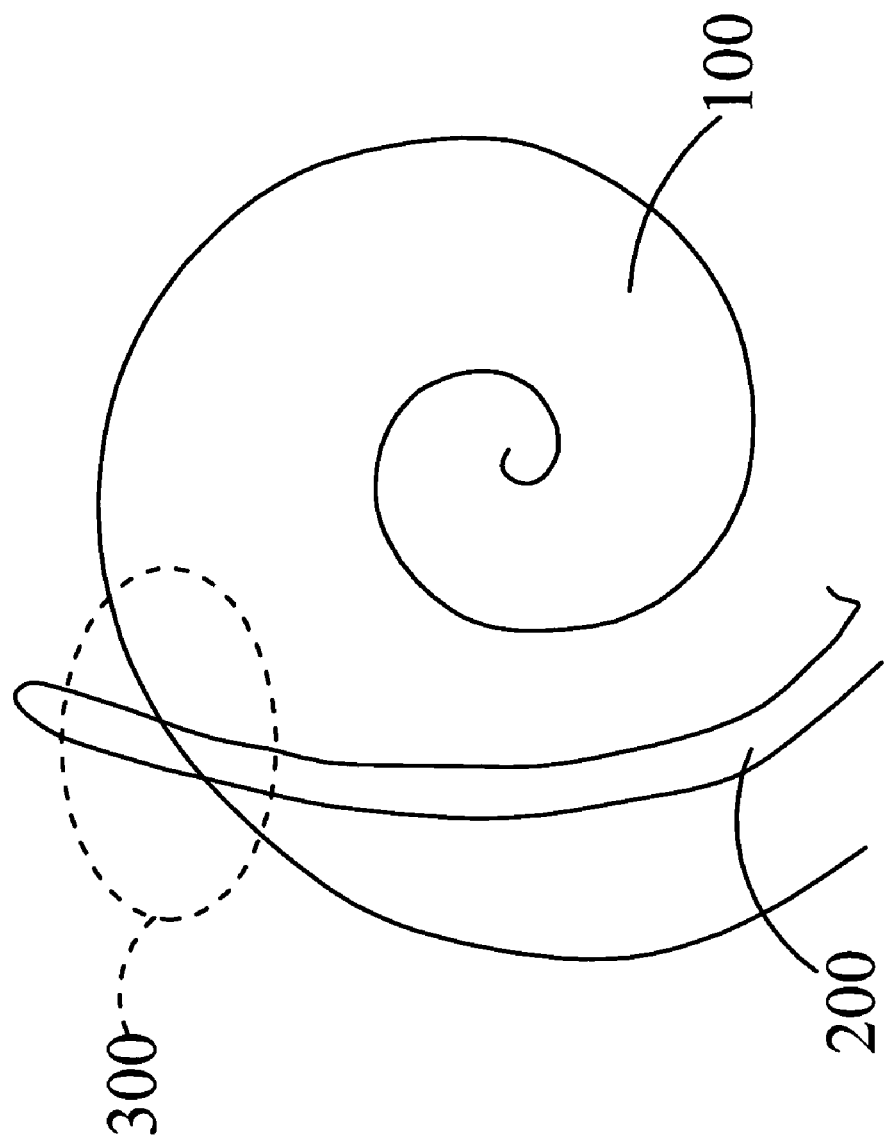
FIG. 1 is a schematic view of a conventional cochlear implant.
Figure 2:
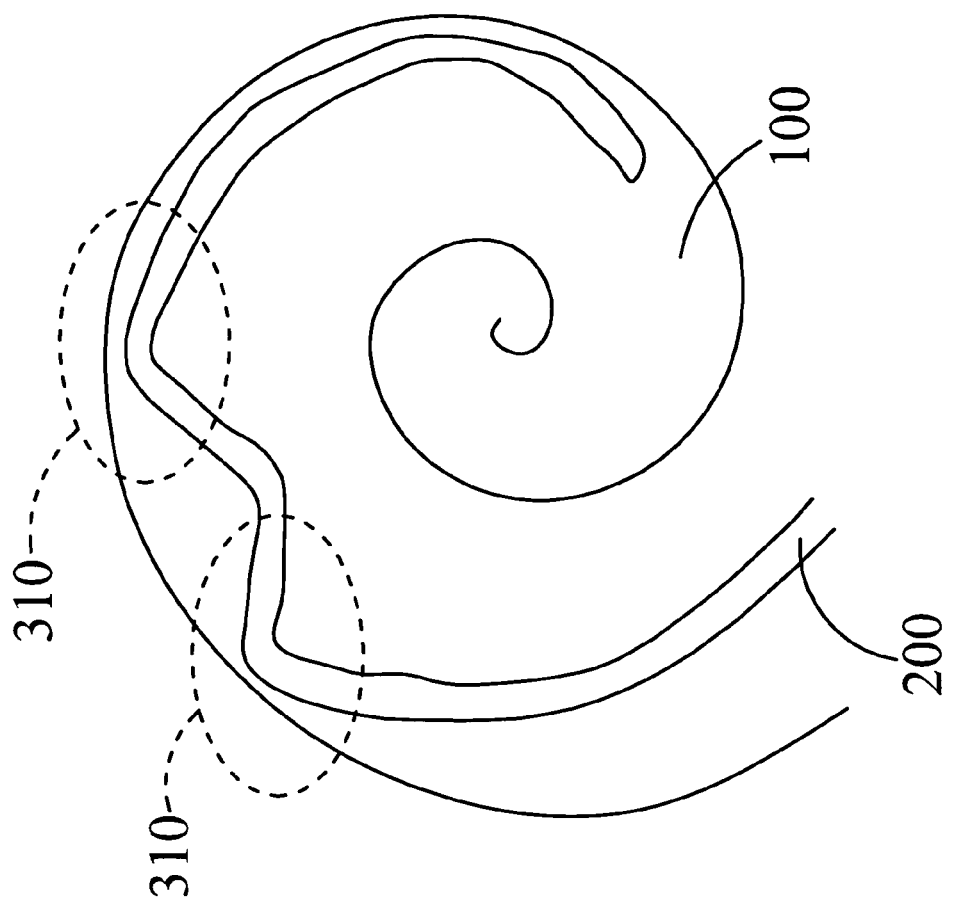
FIG. 2 is another schematic view of the conventional cochlear implant.
Figure 3:
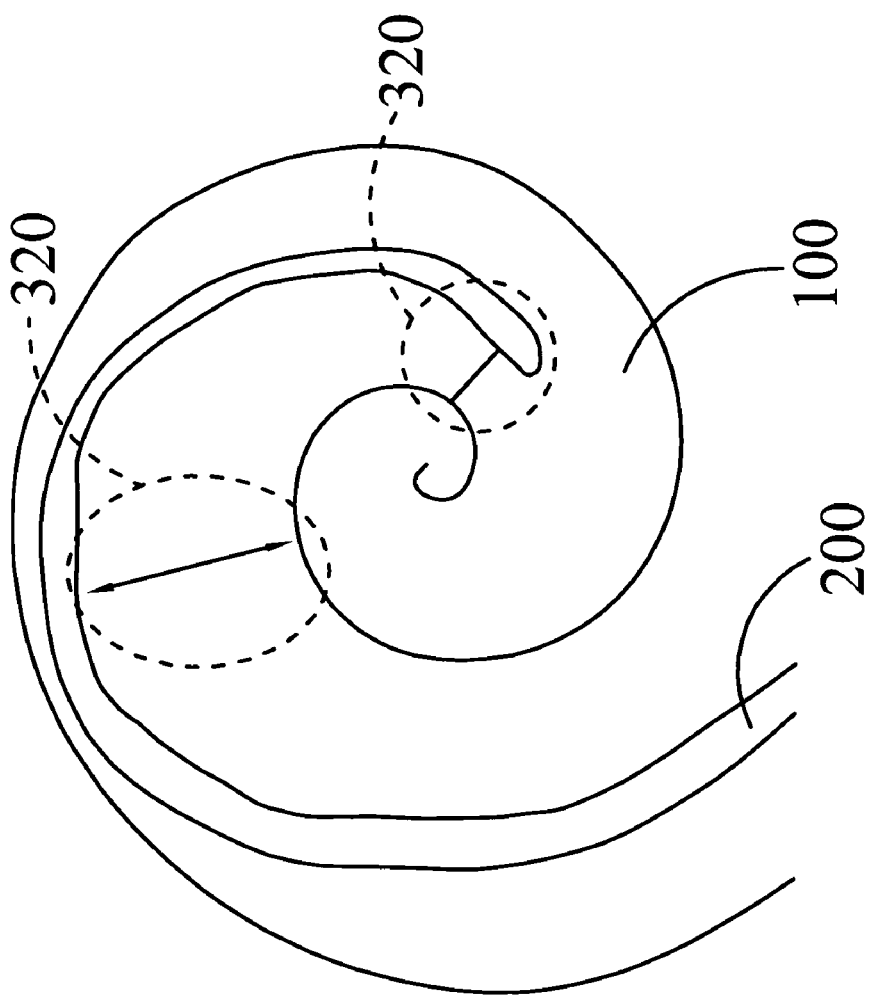
FIG. 3 is still another schematic view of the conventional cochlear implant.
Figure 4:
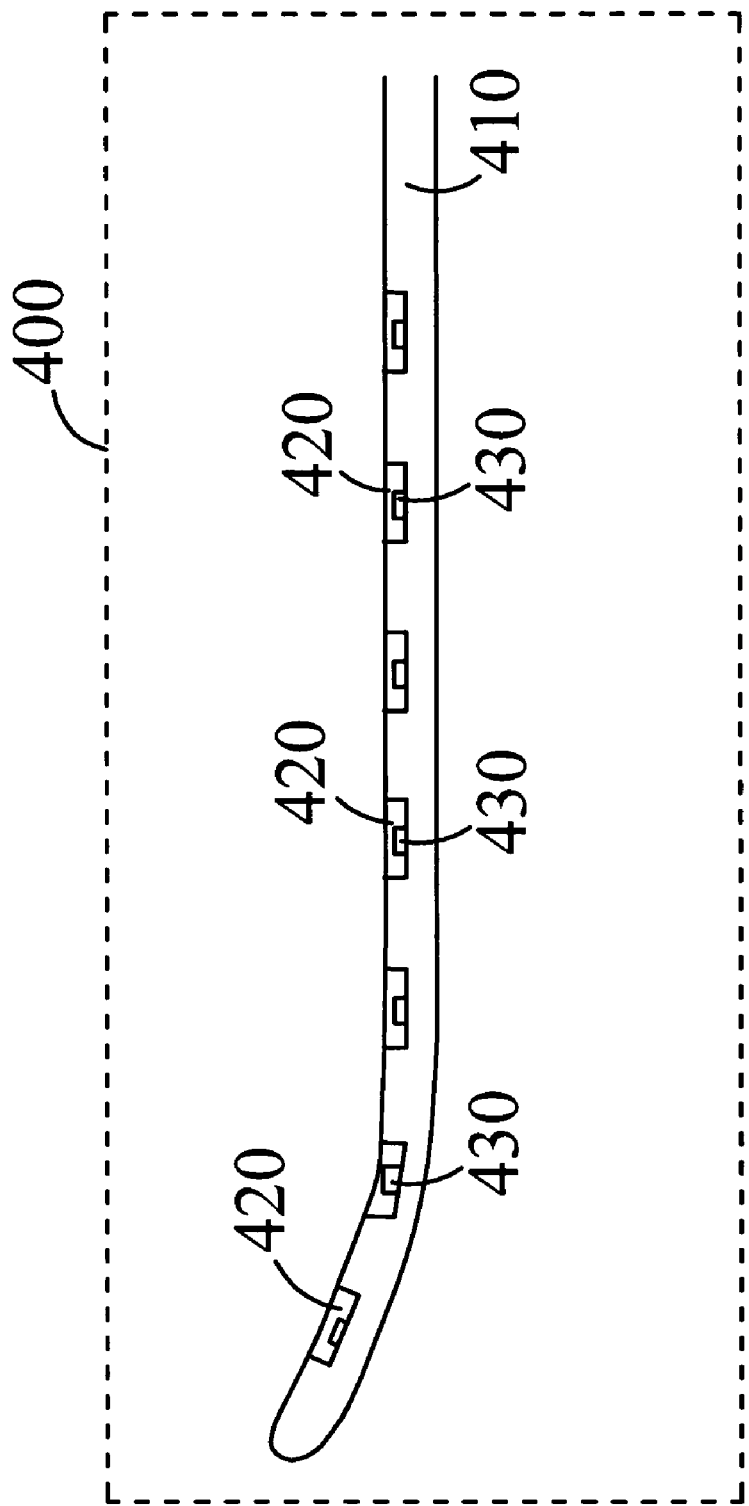
FIG. 4 is a schematic structural diagram of an adjustable implant electrode assembly according to the present invention.

Please refer to FIG. 4 that is a schematic structural diagram of an adjustable implant electrode assembly according to the present invention. As shown, the adjustable implant electrode assembly 400 comprises an implant 410, a plurality of electrodes 420, and a plurality of magnetic components 430. The electrodes 420 are disposed in the implant 410 to provide stimulating currents according to a control signal generated by a control unit (not shown), and the simulating currents can replace bioelectric signals. The magnetic components 430 are combined with the electrodes 420 in one-to-one correspondence for generating a magnetic pole under an excitation current. Therefore, by driving the magnetic pole with an externally applied magnetic field, the implant 410 of the adjustable implant electrode assembly 400 of the present invention can be moved in position.

Figure 5:
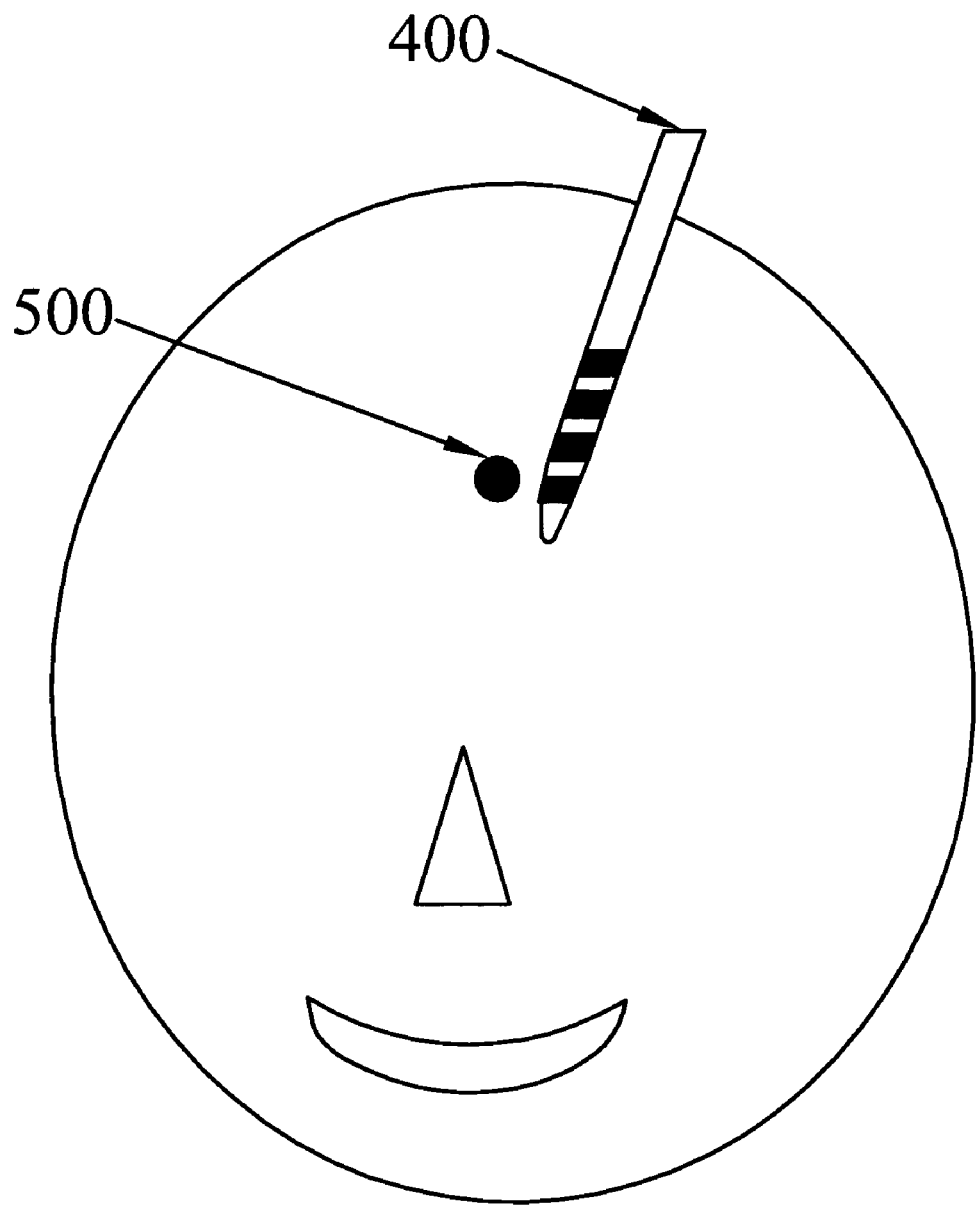
FIG. 5 schematically shows an embodiment of the adjustable implant electrode assembly of the present invention.

Please refer to FIG. 5 that schematically shows an embodiment of the adjustable implant electrode assembly of the present invention. Many of the currently known diseases are caused by abnormal bioelectric signals from brain, such as Parkinson's disease. Therefore, in one embodiment thereof, the adjustable implant electrode assembly 400 of the present invention is a deep brain stimulator for implanting into a patient's deep brain area close to a nidus 500 for providing stimulating currents to suppress the disease caused by electric discharge from abnormal tissues at the nidus 500.

Figure 6:
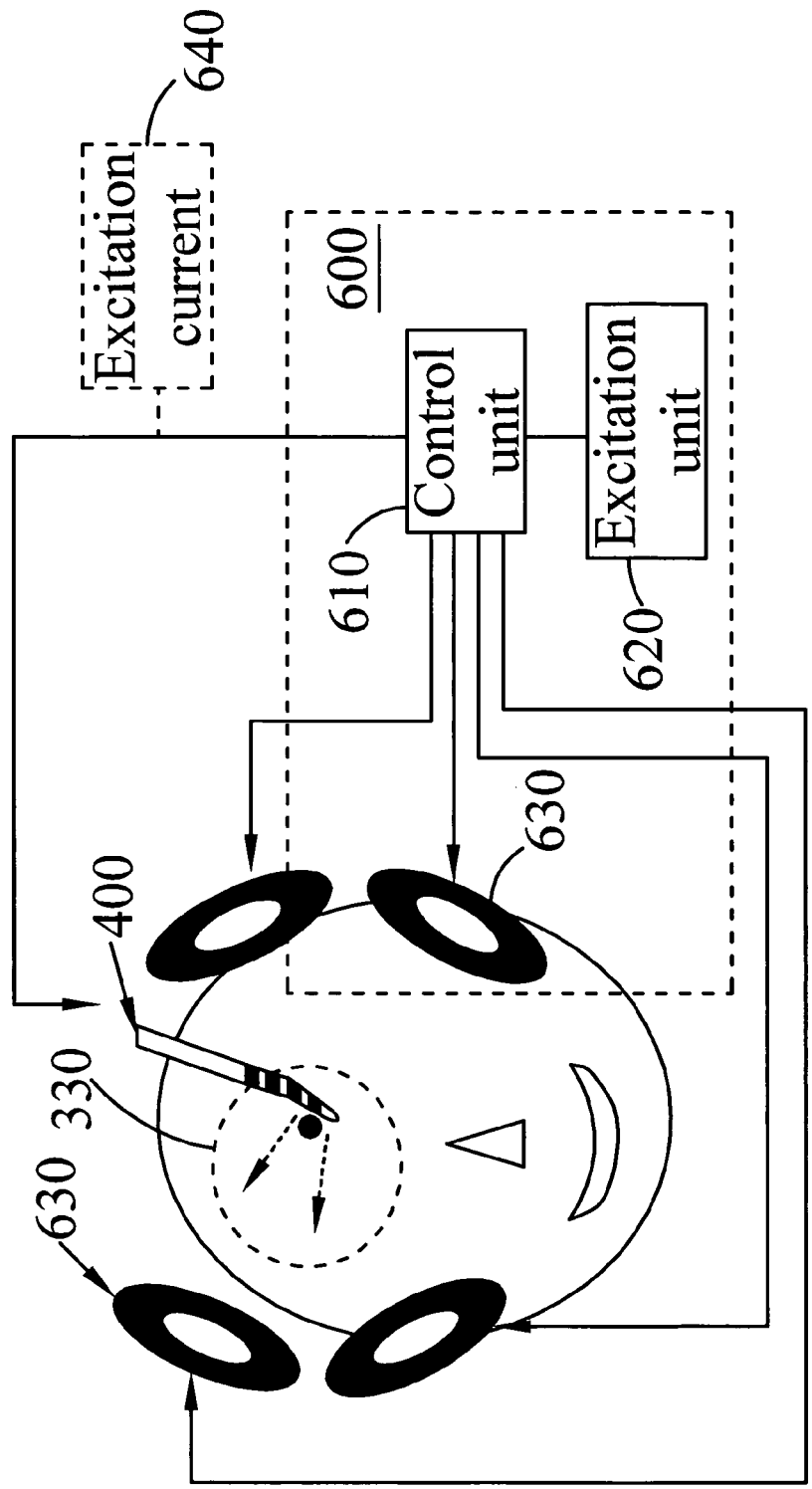
FIG. 6 is a schematic structural diagram of an adjustable implant electrode system according to the present invention.

FIG. 6 is a schematic structural diagram of an adjustable implant electrode system according to the present invention. As shown, the adjustable implant electrode system comprises an adjustable implant electrode assembly 400 and an adjustment device 600 for adjusting the adjustable implant electrode assembly 400 to a desired position. The adjustable implant electrode assembly 400 comprises an implant, a plurality of electrodes, and a plurality of magnetic components, as having been described with reference to FIG. 4. The adjustment device 600 comprises a control unit 610, an excitation unit 620, and one or more magnetic units 630. With the control unit 610, it is able to select one or more magnetic components to be moved from the plurality of magnetic components. The excitation unit 620 is capable of providing an exciting electrical current 640 to turn on the selected one or more magnetic components to be moved, so that the magnetic components that are turned on (selected) will become magnetized and will generate magnetic poles. And, the magnetic unit 630 is capable of generating a magnetic field to drive the magnetic pole, that is, a first magnetically controlled area 330 as indicated in FIG. 6, and thereby move the implant.

Since the brain tissue to be stimulated with deep brain stimulating technique, such as the thalamus, is very small in size, it is very important to implant an implant electrode assembly into a correct position because any deviation of the implant electrode assembly in position would result in poor medical effect. Under this circumstance, in the case of a conventional implant electrode assembly, the implant electrode assembly must be re-implanted, which would very possibly improperly stimulates other body tissues and results in other undesirable side effects. However, with the adjustable implant electrode system of the present invention, a somewhat deviated electrode array, that is, the adjustable implant electrode assembly 400, can be moved in a non-invasive way for the effective electrodes to locate as closer as possible to the nidus 500 to properly stimulate the same without the need of performing the implant surgery operation again. Therefore, the adjustable implant electrode assembly 400 of the present invention can also be used as a non-invasive type deep brain stimulator to be highly valuable in the medical field.

Figure 7:
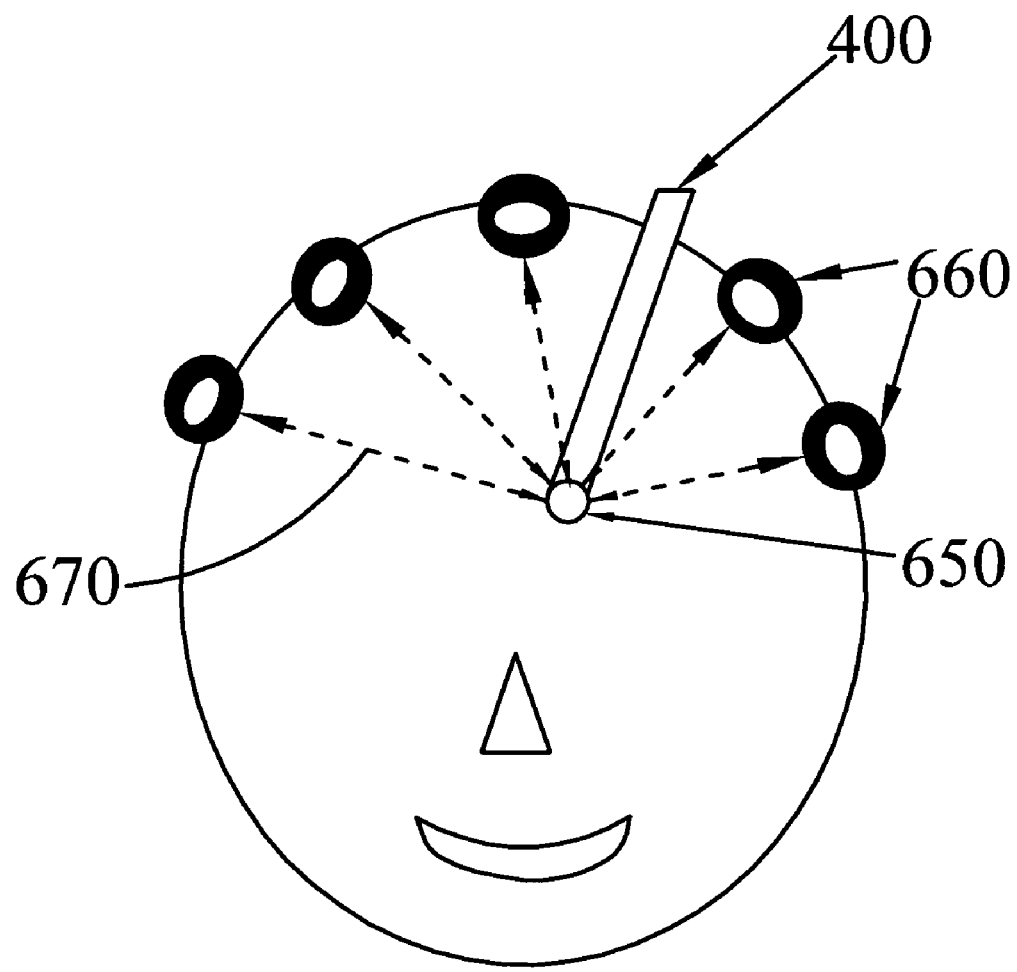
FIG. 7 schematically shows an embodiment of the adjustable implant electrode system of the present invention.

FIG. 7 schematically shows an embodiment of the adjustable implant electrode system of the present invention. As shown, in this embodiment, the adjustable implant electrode assembly 400 has a signal transceiver source 650 provided at a head end thereof, and a plurality of external signal transceivers 660 is mounted on a patient's head. The external signal transceivers 660 can be, for example, coils. The signal transceiver source 650 is caused to transmit a detection signal 670, such as a magnetic pulse. Then, difference in the time at which each of the external signal transceivers 660 receives the detection signal 670 is calculated to determine an exact position of the signal transceiver source 650 in the brain. In this manner, the head end position of the adjustable implant electrode assembly 400 can be adjusted at any time during the implant surgery operation. Similarly, the detection signal can be otherwise transmitted in a reverse direction. In this case, the external signal transceivers 660 mounted on the patient's head serve as signal transmitters and the signal transceiver source 650 provided at the head end of the implant electrode assembly 400 serves as a signal receiver. Then, the external signal transceivers 660 are caused to respectively transmit a detection signal 670, which is received by the signal transceiver source 650. Then, difference in the time at which the signal transceiver source 650 receives each of the detection signals 670 transmitted by the external signal transceivers 660 is calculated to determine the exact position of the head end of the implant electrode assembly 400. For the purpose of distinguishing the detection signals 670 from one another and identifying the transmission source of each of these detection signals 670, the external signal transceivers 660 are caused to transmit a specific detection signal each. For example, the detection signals 670 each can be a signal having a different pulse width; or, the detection signals 670 each can be transmitted in a particularly encoded pulse pattern. Therefore, according to this embodiment, the adjustable implant electrode system of the present invention is able to obtain position information provided by the adjustable implant electrode assembly 400 to thereby enable an upgraded accuracy in the implant surgery operation.

Figure 8:
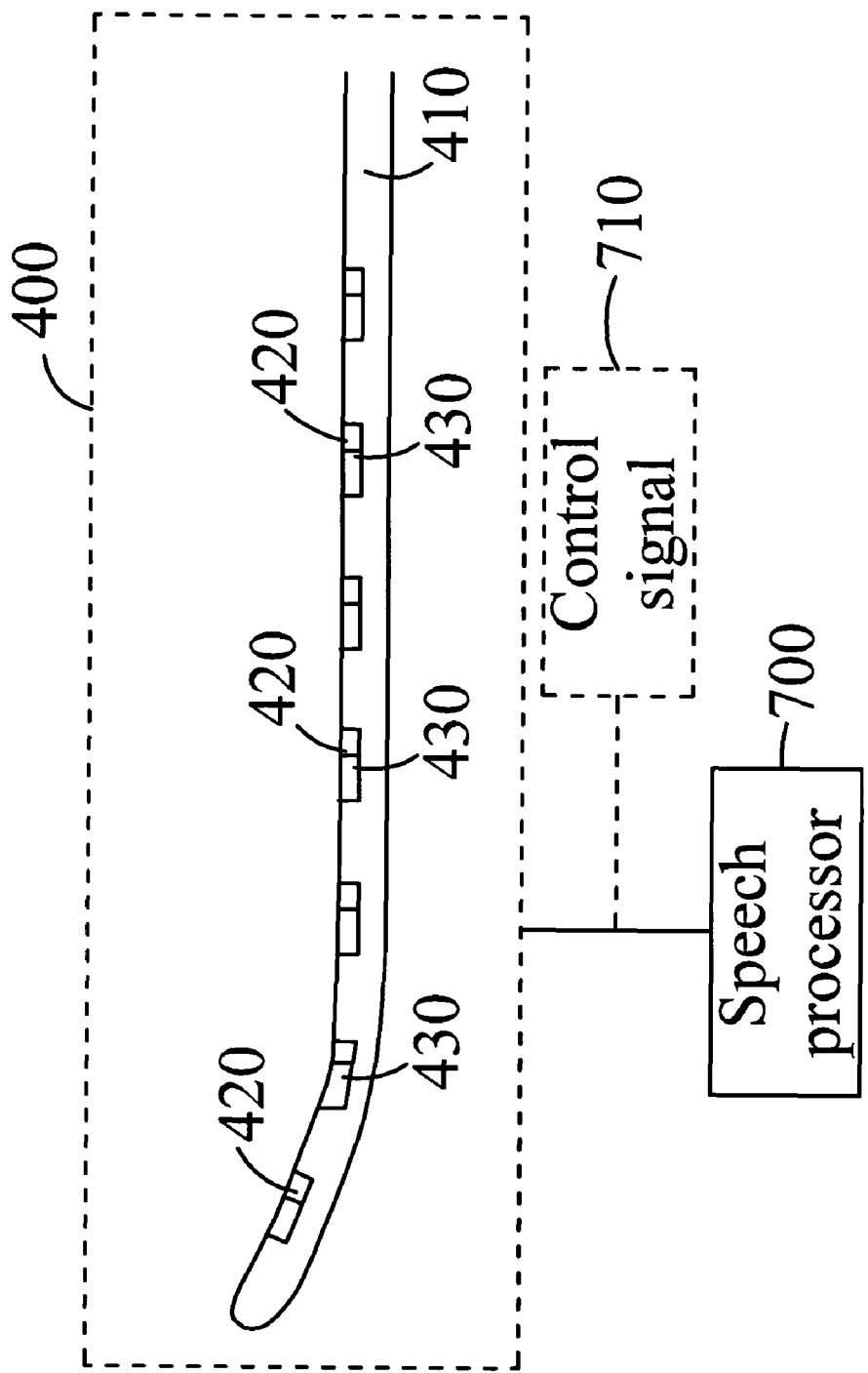
FIG. 8 is a schematic structural diagram of an adjustable cochlear implant as an embodiment of the present invention.

FIG. 8 is a schematic structural diagram of an adjustable cochlear implant as an embodiment of the adjustable implant electrode assembly 400 of the present invention. As shown, in this embodiment, a speech processor 700 is externally connected to the adjustable implant electrode assembly 400 for providing a control signal 710 to drive a desired one of the electrodes 420 to produce a stimulating current. What is noted is the magnetic components 430 are preferably embedded in the electrodes 420, so that an externally applied magnetic field can accurately move a desired electrode 420 when driving the magnetic component 430 corresponding to that electrode 420. Of course, the magnetic components 430 are not necessarily embedded in the electrodes 420. And, according to another operable embodiment of the present invention, the magnetic components 430 can be otherwise joined to one side of the electrodes 420 in one-to-one correspondence. Moreover, the implant 410 is a flexible member commonly used to manufacture a cochlear implant, the material thereof must meet the medical-grade quality standard. Therefore, a highly stable, non-toxic, bio-compatible, and soft resin material is selected for making the implant 410. The magnetic components 430 each are used to generate a magnetic pole under an excitation current. Therefore, the magnetic components 430 can be made of electrical coils or any magnetically guidable materials, such as iron, cobalt, nickel, or any combination thereof.

Figure 9:
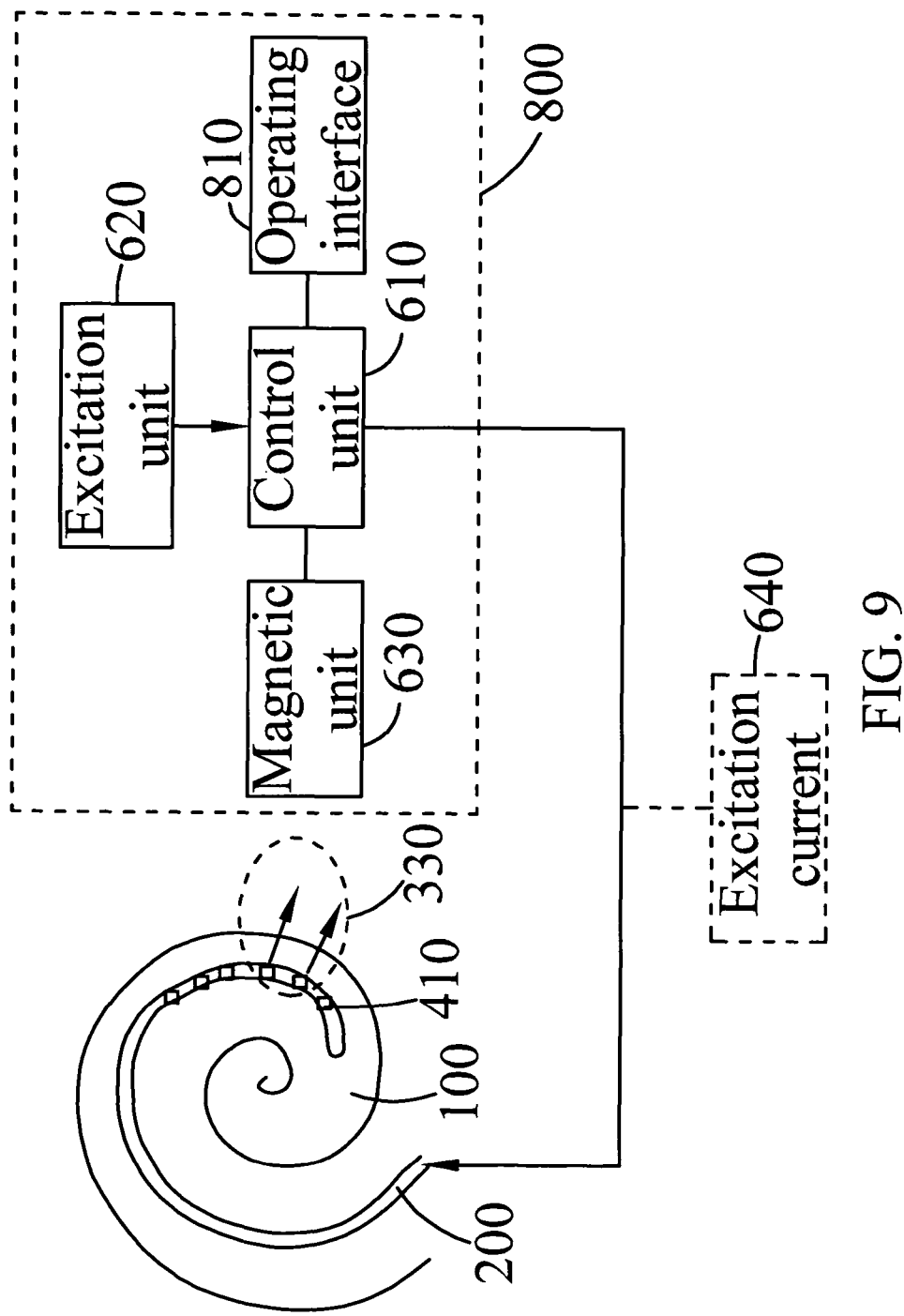
FIG. 9 is a schematic structural diagram of an adjustable cochlear implant system as an embodiment of the present invention.

Please refer to FIG. 9 that is a schematic structural diagram of an adjustable cochlear implant system as an embodiment of the present invention. As shown, the adjustable cochlear implant system comprises an adjustable cochlear implant 200 and an adjustment device 800. The cochlear implant 200 can be an embodiment of the adjustable implant electrode assembly 400 of the present invention, and the adjustment device 800 is adapted to adjust the adjustable cochlear implant 200 in position. The adjustable cochlear implant 200 comprises an implant 410, a plurality of electrodes, and a plurality of magnetic components. The electrodes are disposed in the implant 410 to provide stimulating currents according to a control signal for replacing bioelectric signals. The implant 410 can be a flexible member, and the magnetic components are combined with the electrodes in one-to-one correspondence. The adjustment device 800 comprises a control unit 610, an excitation unit 620, and one or more magnetic units 630. With the control unit 610, it is possible to select one or more magnetic components to be moved from the plurality of magnetic components. The excitation unit 620 is capable of providing an exciting electrical current 640 to turn on the selected one or more magnetic components to be moved, so that the magnetic components that are turned on (selected) will become magnetized and will generate magnetic poles. And, the magnetic unit 630 is capable of generating a magnetic field to drive the magnetic pole to thereby move the implant 410. The adjustable cochlear implant system in this embodiment can further comprise an operating interface 810, via which a surgeon performing the implant surgery operation selects the magnetic component to be moved and accurately moves the magnetic unit 630 to push or pull the magnetic component to be moved, and thereby adjusts the cochlear implant 200 to a desired position.

Figure 10:
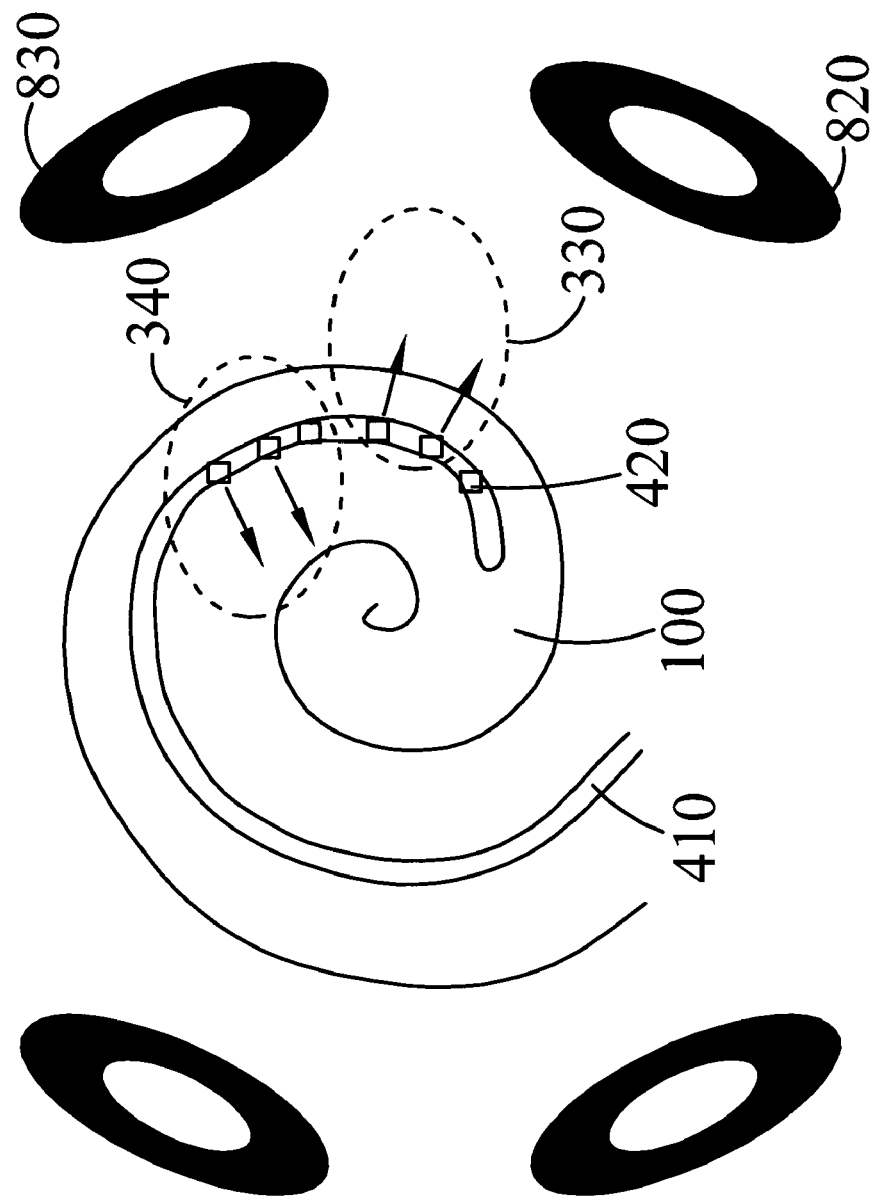
FIG. 10 schematically shows an embodiment of the adjustable cochlear implant system according to the present invention.

FIG. 10 schematically shows an example of the adjustable cochlear implant system according to the present invention. As shown, the magnetic unit 630 can comprise a plurality of magnetic coils. A first one of the magnetic coils as denoted by reference numeral 820 is able to pull a first magnetically controlled area 330 relative to a cochlear axis of a patient's cochlea, while a second magnetic coil 830 is able to push a second magnetically controlled area 340 relative to the cochlear axis. Of course, it is also possible to move a magnetically controlled area located between two magnetic coils by a resultant force produced through controlling the magnetic forces of the two magnetic coils or even other magnetic coils. Therefore, the adjustable cochlear implant system of the present invention utilizes magnetic fields to perform fine adjustment of electrode positions to thereby enable a non-invasive cochlear implant fine adjustment operation.

Moreover, when an electrode 420 for a relatively important band or an electrode 420 located at a position with the auditory nerve in a relatively good condition becomes damaged, the adjustable cochlear implant system according to the present invention can utilize a magnetic field to shift another adjacent electrode 420 from a less important band or another electrode 420 located at a position with the auditory nerve in a relatively poor condition to thereby replace the damaged electrode 420. Therefore, it is not necessary to perform the cochlear implant surgery operation again. The magnetic components are preferably embedded in the electrodes 420, so that the externally applied magnetic fields can accurately move desired electrodes 420 when moving the magnetic components 430 corresponding to the electrodes 420. Of course, the magnetic components 430 are not necessarily embedded in the electrodes 420. And, according to another operable embodiment of the present invention, the magnetic components can be otherwise joined to one side of the electrodes 420 in one-to-one correspondence. Moreover, the implant 410 must be made of a material meeting the medical-grade quality standard. Therefore, a highly stable, non-toxic, biocompatible, and soft resin material is selected for making the implant 410. The magnetic components each are used to generate a magnetic pole under an excitation current. Therefore, the magnetic components can be made of electrical coils or any magnetically guidable materials, such as iron, cobalt, nickel, or any combination thereof. What is noted is, in the case the magnetic components are electromagnets made of any of the above-mentioned materials, the adjustable cochlear implant system of the present invention can further excite and demagnetize one or more electromagnets corresponding to selected electrode or electrodes 420, so as to accurately control the position of the implanted adjustable cochlear implant.

Figure 11:
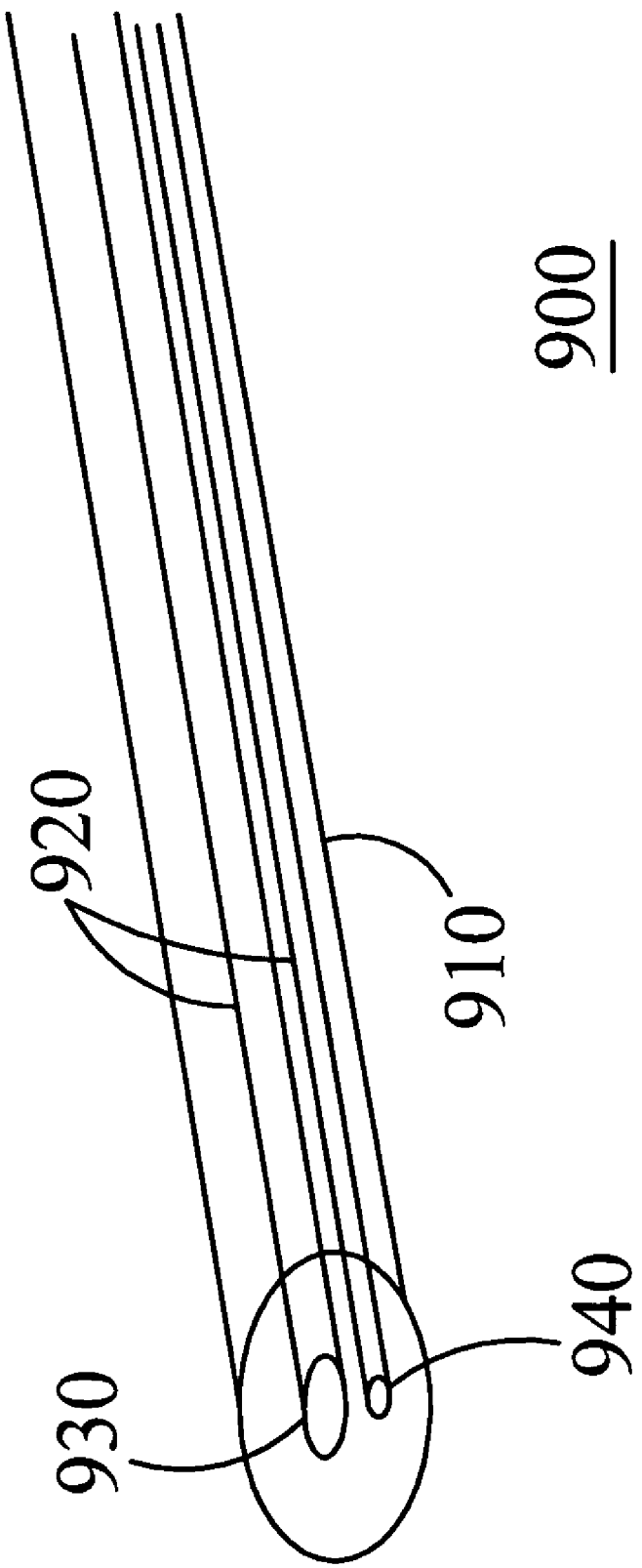
FIG. 11 schematically shows an embodiment of an endoscope unit for use with the adjustable implant electrode system according to the present invention.

FIG. 11 schematically shows an embodiment of an endoscope unit for use with the adjustable implant electrode system according to the present invention. Since the electrode array is located inside a patient's body during an implant surgery operation, such as in the cochlea or in the brain, it is very difficult for the surgeon to clearly know the exact position of the electrode array while performing the operation. The implant might be incorrectly positioned to impair internal body tissues. While there are external medical imaging instruments available for monitoring and controlling the implantation, such imaging instruments have adverse influences on human body and do not always have high accuracy. Therefore, according to another embodiment of the present invention, the adjustable implant electrode assembly 400 is further provided with an endoscope unit 900, so that images of areas deep in the cochlea or the brain in the process of implant surgery operation can be transmitted via an optical fiber to the surgeon performing the operation. Please refer to FIG. 11. According to the illustrated embodiment, the endoscope unit 900 comprises an endoscope carrier 910, in which there are provided two optical fibers 920. One of the two optical fibers 920 is connected to an endoscope 930, while the other optical fiber 920 is used to provide an illumination source 940.

What is claimed is:

1. An adjustable implant electrode assembly, comprising:
   an implant
   a plurality of electrodes disposed in the implant for providing stimulating currents according to a control signal; and
   a plurality of magnetic components disposed in the implant and combined with the plurality of electrodes in one-to-one correspondence;
   wherein, the magnetic components are embedded in the electrodes in one-to-one correspondence.

2. The adjustable implant electrode assembly as claimed in claim 1, wherein the magnetic components are made of electrical coils or a material selected from the group consisting of iron, cobalt, nickel, and any combinations thereof.

3. The adjustable implant electrode assembly as claimed in claim 1, wherein the adjustable implant electrode assembly is selected from the group consisting of a cochlear implant and a deep brain stimulator.

4. The adjustable implant electrode assembly as claimed in claim 3, further comprising a speech processor for providing the control signal.

5. The adjustable implant electrode assembly as claimed in claim 3, wherein the implant is a flexible member.

6. The adjustable implant electrode assembly as claimed in claim 5, wherein the flexible member is made of a soft resin material.

7. The adjustable implant electrode assembly as claimed in claim 3, wherein the implant further comprises an endoscope unit.

8. The adjustable implant electrode assembly as claimed in claim 1, further comprising a signal transceiver source located at a head, end of the implant for receiving or transmitting a detection signal to thereby provide position information about the implant.

9. An adjustable implant electrode system, comprising:
   an adjustable implant electrode assembly, which comprises:
   an implant;
   a plurality of electrodes disposed in the implant for providing stimulating currents according to a control signal; and
   a plurality of magnetic components disposed in the implant and combined with the plurality of electrodes in one-to-one correspondence; and
   an adjustment device for adjusting the adjustable implant electrode assembly to a desired position, the adjustment device comprises:
   a control unit for selecting one or more magnetic components to be moved from the plurality of magnetic components;
   an excitation unit for exciting the selected one or more magnetic components to be moved, so that the one or more magnetic components generate a magnetic pole; and
   one or more magnetic units capable of generating a magnetic field to drive the magnetic pole and thereby move the implant;
   wherein, the magnetic components are embedded in the electrodes in one-to-one correspondence.

10. The adjustable implant electrode system as claimed in claim 9, wherein the magnetic components are made of electrical coils or a material selected from the group consisting of iron, cobalt, nickel, and any combinations thereof.

11. The adjustable implant electrode system as claimed in claim 9, wherein the magnetic components each are an electromagnet, and wherein the excitation unit is able to excite and demagnetize the magnetic components.

12. The adjustable implant electrode system as claimed in claim 9, wherein the magnetic unit is a magnetic coil.

13. The adjustable implant electrode system as claimed in claim 9, wherein the adjustable implant electrode system is selected from the group consisting of a cochlear implant system and a deep brain stimulating system; and the adjustable implant electrode assembly is selected from the group consisting of a cochlear implant and a deep brain stimulator in correspondence to the cochlear implant system and the deep brain stimulating system, respectively.

14. The adjustable implant electrode system as claimed in claim 13, further comprising a speech processor for providing the control signal.

15. The adjustable implant electrode system as claimed in claim 13, wherein the implant is a flexible member.

16. The adjustable implant electrode system as claimed in claim 15, wherein the flexible member is made of a soft resin material.

17. The adjustable implant electrode system as claimed in claim 13, wherein the implant further comprises an endoscope unit.

18. The adjustable implant electrode system as claimed in claim 9, further comprising a signal transceiver source and a plurality of external signal transceivers, the signal transceiver source being located at a head end of the implant, and the signal transceiver source and the external signal transceivers each being adapted to receive and transmit a detection signal to thereby provide position information about the implant.

* * * * *